Figure 1:
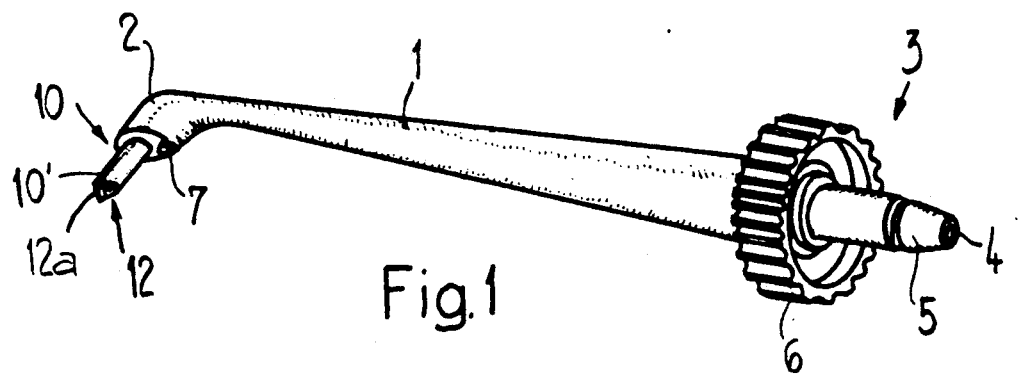

United States Patent [19]

Fischer

[11] Patent Number: 5,273,428
[45] Date of Patent: Dec. 28, 1993

[54] CLEANING NOZZLE FOR DENTAL HYGIENE

[75] Inventor: Franz Fischer, Triengen, Switzerland

[73] Assignee: Trisa Buerstenfabrik AG Triengen, Triengen, Switzerland

[21] Appl. No.: 543,726

[22] PCT Filed: Dec. 7, 1989

[86] PCT No.: PCT/CH89/00214

§ 371 Date: Oct. 9, 1990

§ 102(e) Date: Oct. 9, 1990

[87] PCT Pub. No.: WO90/06091

PCT Pub. Date: Jun. 14, 1990

[30] Foreign Application Priority Data

Dec. 8, 1988 [CH] Switzerland ............... 4537/88

[51] Int. Cl.⁵ ........................................ A61G 17/02
[52] U.S. Cl. ........................................ 433/80; 433/82
[58] Field of Search ............... 433/80, 141, 215, 82, 433/216; 132/308; 128/62.4; 401/136, 284

[56] References Cited

U.S. PATENT DOCUMENTS

| | | | |
|---|---|---|---|
| 180,985 | 8/1876 | Birtwistle | 401/284 |
| 913,184 | 2/1909 | Alexander | 401/284 X |
| 1,336,604 | 4/1920 | Baker | 401/284 |
| 1,663,439 | 3/1928 | Christianson | 401/284 |
| 1,674,207 | 6/1928 | Krill | 401/284 |
| 2,705,335 | 4/1955 | Glassman et al. | 401/284 X |
| 3,256,604 | 6/1966 | Borden | |
| 3,356,095 | 12/1967 | Tylle | 401/284 X |
| 3,400,999 | 9/1968 | Goldstein | 128/62 A |
| 3,428,404 | 2/1969 | Ciancio | 401/284 X |
| 3,537,444 | 11/1970 | Garn | 128/66 |
| 3,547,110 | 12/1970 | Balamuth | 128/66 |
| 3,610,234 | 10/1971 | Oates | 128/66 |
| 3,939,520 | 2/1976 | Axelsson | 132/308 X |
| 4,340,366 | 7/1982 | Heil | 433/82 |
| 4,387,479 | 6/1983 | Kigyos | 132/308 X |
| 4,564,005 | 1/1986 | Marchand et al. | 128/66 |
| 4,808,109 | 2/1989 | Thornton | 433/80 X |

FOREIGN PATENT DOCUMENTS

| | | |
|---|---|---|
| 2432854 | 1/1976 | Fed. Rep. of Germany ........ 128/66 |
| 8424911 | 12/1985 | Fed. Rep. of Germany . |
| 8809217 | 10/1988 | Fed. Rep. of Germany . |
| 2288495 | 5/1976 | France . |
| 667382 | 10/1988 | Switzerland . |

Primary Examiner—Gene Mancene
Assistant Examiner—Nicholas D. Lucchesi
Attorney, Agent, or Firm—Keck, Mahin & Cate

[57] ABSTRACT

A dental cleaning nozzle has a brush element combined with a water jet. The jet is directed to provide interaction with the brush element with a part of the jet bypassing the end of the brush element. The arrangement enhances plaque removal.

11 Claims, 3 Drawing Sheets

CLEANING NOZZLE FOR DENTAL HYGIENE

The present invention concerns a cleaning nozzle according as well as a dental care instrument provided with such a cleaning nozzle.

Such cleaning nozzles are used individually and are removably connectable to a base instrument which is equipped with a water tank and water pump and which supplies the nozzle with water through a water feed line. Food residues in gum pockets and gaps between the teeth can be reliably flushed out by the jet of water produced by the nozzle. Even in poorly accessible places very good tooth cleaning is possible with it. The water jet which, depending on the base instrument, can be regulated in intensity, also massages the gums. As a result the perfusion of the gums is stimulated, which helps to strengthen sensitive gums and counteracts gum shrinkage.

Although these advantages have been confirmed, it has been found that dental plaque already present cannot be removed to a sufficient degree by the water jet. Therefore despite the proper use of a cleaning nozzle of the type described, the formation of tartar as a result of the adhering plaque cannot be avoided; the teeth are not completely cleaned.

Accordingly, it is the object of the present invention to devise a cleaning nozzle for dental care with improved action which, besides an advantageous effect on the gums, also makes complete cleaning of the teeth possible especially in poorly accessible places.

To solve this problem, in the cleaning nozzle according to the invention, a brushing element is arranged with respect to the path of the water jet in such a way that the water jet passes at least partially freely by the brushing element and is therefore not atomized on it, the dental plaque is detached and removed by the interaction of the water jet and the bristles of the brush element on the tooth surface. The continually acting water jet can attack and totally remove the parts of the plaque that were only loosened up by the action of the brush.

Particles freshly detached, whether by the bristles or the water jet, are immediately flushed out of the brush region and into the mouth cavity. This is important for complete tooth cleaning. Remaining components of the dental plaque could otherwise be transported further by the brush still kept in motion by the user) e.g. into the next gap or gum pocket. Plaque material pushed back and forth by the bristles is also preferentially deposited in carious depressions and thus accelerates tooth decay.

As a result of the water jet's passing at least partially by the brush element, food residues are flawlessly flushed out of the even poorly accessible places and the gum is massaged so that flawless and complete cleaning with a salutary effect on the gums is provided.

Preferred versions of the cleaning nozzle according to the invention have the features of the dependent claims. Various versions of the cleaning nozzles according to the invention are illustrated below with reference to the figures.

FIG. 1 shows a perspective view of a cleaning nozzle.

Figure 2:
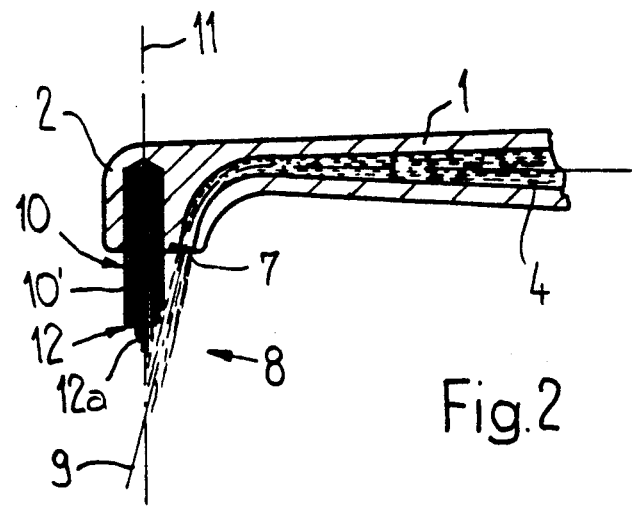
Figure 3:
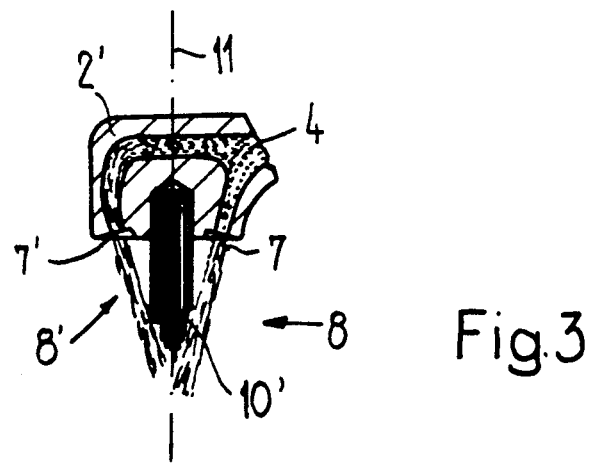

FIG. 2 is a longitudinal section through the end of the nozzle in FIG. 1 showing the nozzle outlet, FIG. 3 is a longitudinal section through the end of another version of the cleaning nozzle showing the nozzle outlet, and FIGS. 4 through 9 each show a longitudinal section through the end of other versions of the cleaning nozzle with replaceable brushing elements, showing the outlet end of the nozzle.

The cleaning nozzles shown in FIGS. 1 and 2 consists of a nozzle body with a head 2 and a coupling part 3.

The coupling part 3 has a connecting pin 5 with an interior water channel 4 and can be plugged into a water supply line of a basic dental care instrument, not shown, equipped with a pump. To facilitate handling, the nozzle body 1 is provided with a handle part 6.

The nozzle body 1 is designed as a cannula whose water channel 4 runs to a nozzle exit 7 arranged in a head 2 which is designed in such a way that it produces a directed water jet 8 with a longitudinal axis 9 (FIG. 2). Also in the head is a brush element 10 arranged close to the nozzle outlet 7 with a bristle bundle 10' of round cross section whose longitudinal axis is denoted by 11 (FIG. 2). It has a pointed end 12 with a conical end plane 12a. The head 2 is bent away with respect to the remaining part of the nozzle body 1 which allows the user to clean on all sides, even the back teeth situated to the rear of the mouth cavity.

FIG. 2 shows a longitudinal section through the head end of the nozzle body 1. The channel 4 in accordance with the bending of the head 2 runs in a curve to the nozzle outlet 7 which generates a water jet 8 whose axis 9 runs at an acute angle to the axis 11 of the brush element 10 or the bristle bundle 10'. The bristle bundle 10' operating in the action zone of the water jet 8 touches the jet with its end face 12a. With the pointed end 12 of the bristle bundle 10' even narrow gaps between the teeth or, e.g., the neck of the tooth at the transition to the gum can be cleaned. Although the bristle bundle 10' operates in the zone of action of the water jet 8, the latter essentially passes by it undisturbed so that it strikes the surface of the tooth with full intensity carrying away only the loosened up plaque parts and can remove the detached material from the region of the brush before it can be pushed on by the bristle bundle 10' and be deposited in an undesirable location.

FIG. 3 shows the modified head 2' of another version of the cleaning nozzle which is advantageous for certain applications In the head 2' another nozzle outlet 7' is provided and designed in such a way that the water jet 8' emitted by it displays the same geometrical relationships with respect to the bristle bundle 10' as the jet 8 of the nozzle outlet 7. With this the action zone of the water jet 8, 8' becomes larger, which is advantageous for cleaning the rearmost back teeth which must be undertaken blindly.

Figure 4:
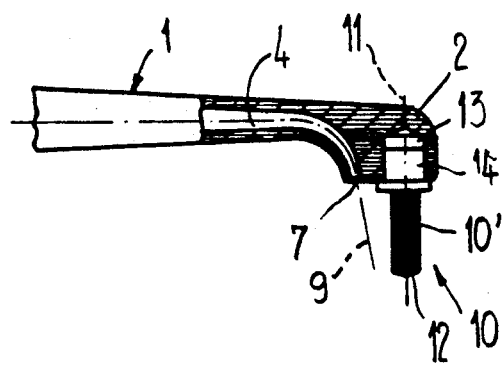
Figure 5:
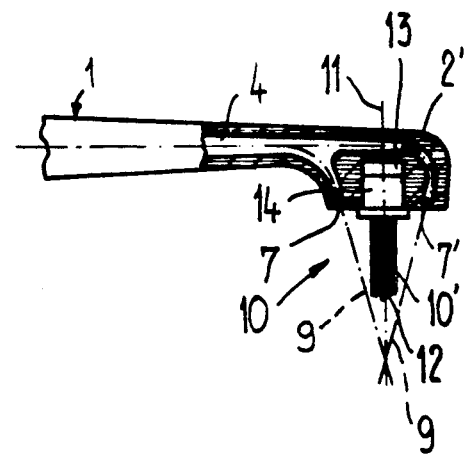
Figure 6:
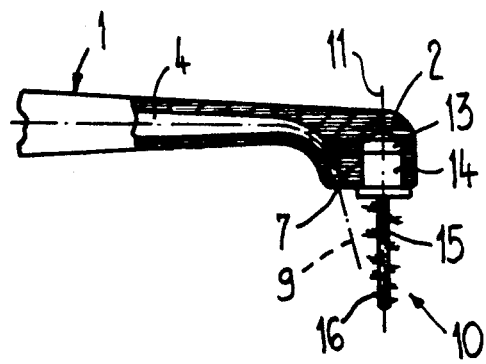
Figure 7:
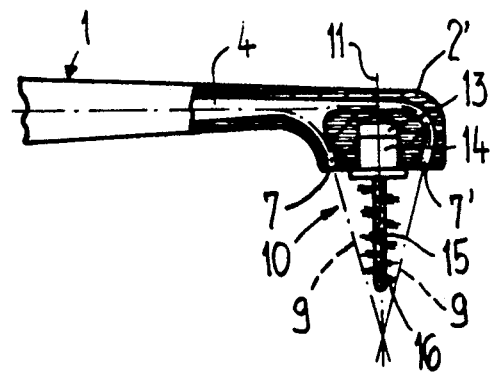

FIGS. 4 through 9 show other versions of the cleaning nozzle in which the design of the head 2 in FIGS. 4, 6, 8 and 9 corresponds to the design of the head 2 shown in FIG. 2, and the design of the head 2' in FIGS. 5 and 7 essentially corresponds to the head 2' in FIG. 3. The design of the channel 4 and the nozzle exit 7 and 7' will not be discussed further. The water jet is indicated in these figures by its longitudinal axis 9 and the longitudinal axis of the brush element 10 is denoted by 11.

In the version shown in FIGS. 4 through 7 in the head 2, 2' of the nozzle body 1 a blind hole 13 is provided whose axis coincides with the longitudinal axis 11 of the brush element 10. In the blind hole 13 a cylindrical bushing 14 is inserted. In the version shown in FIGS. 4 and 5, a bristle bundle 10' is anchored in the bushing 14 which corresponds to the bristle bundle 10' of the variation shown in FIGS. 1 through 3. In the version shown in FIGS. 6 and 7, a carrier organ 15 for the bristles 16 of a brush element 10 is mounted in the bushing 14. The carrier organ 15 consists, for example, of 2 twisted-together wires between which the bristles 16 standing out in the radial direction with respect to the longitudinal axis 11 are arranged. The bristles 16 are held in place as a result of the twist of these wires, and a meandering arrangement of the bristles 16 is achieved, as may be recognized from FIGS. 6 and 7.

The bushing 14 is removably held in the head 2 so that different brush elements 10 can be exchanged for one another or a worn brush element 10 can be replaced by a new one.

Figure 8:
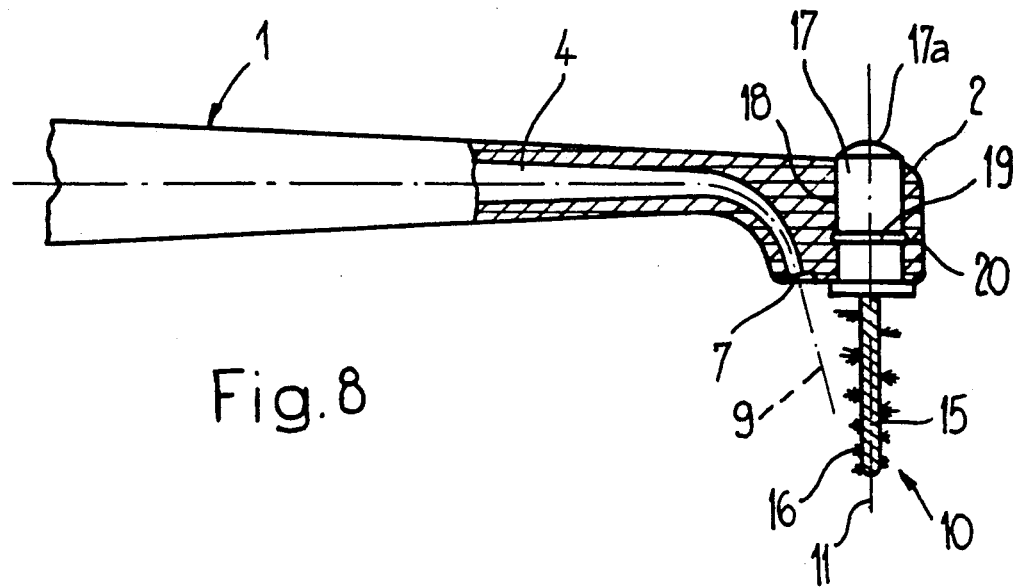
Figure 9:
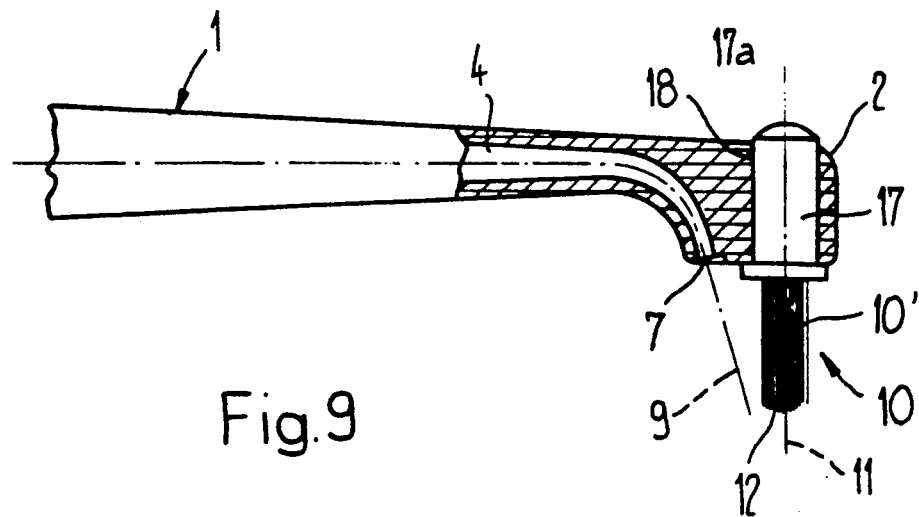

The 2 versions shown in FIGS. 8 and 9 differ from those in FIGS. 6 and 4 in the different type of holding of the brush element 10 in the head 2.

The carrying organs 15 for the bristles 16 (FIG. 8) or the bristle bundle 10 (FIG. 9) are anchored in a cylindrical holding part 17 which extends through a throughgoing boring 18 in the head 2 and is removeably held in it in a suitable way. In FIGS. 8 and 9 two possible especially simple designs for mounting the holding part 17 in the head 2 are shown.

In the version shown in FIG. 8 the holding part 17 has an annular bead 19 which engages the annular groove 20 in the head 2. This interlocking connection can also be designed in a different way.

As opposed to this in the variation shown in FIG. 9 the holding part 17 is held in the head 2 by frictional lock.

In both versions the holding part 17 is provided with a rounding 17a at its upper end which extends a little past the head 2. By pressing on this rounding 17a the holding part 17 can be forced out of the boring 18.

Note that in all versions of the cleaning nozzle the longitudinal axis 9 of the water jet 8, 8' passes by the free end 12 of the brush element 10.

In another version, as opposed to the versions shown with two nozzle outlets 7, 7', a single nozzle outlet encircling the brush element can be provided.

It is also possible to arrange the end of the brush element immediately next to the water jet for extending into the water jet. A condition, however, is that the brushing takes place in the zone of the action of the water jet and that the latter passes freely by the end of the brush element, i.e. is not disturbed and that as a result its intensity is sufficient for removing loosened up dental plaque and flushing the particles out of the brush region.

The coupling part can be provided with other conventional connecting means instead of the plug-in pin, e.g., depending on the design of the water supply line.

What is claimed is:

1. A cleaning nozzle for dental care comprising a nozzle body having two opposite ends, a single non-driven brush element attached to the nozzle body at one end of the nozzle body, said single brush element having a longitudinal axis and a free end protruding from the nozzle body, said nozzle body further comprising at least one nozzle outlet arranged adjacent the brush element for emitting a water jet, a coupling provided at the other end of the nozzle body for detachably connecting the nozzle body to a water supply line and conduit means arranged between the coupling and the at least one nozzle outlet for connecting the at least one nozzle outlet with the water supply line, the at least one nozzle outlet having a longitudinal axis defining the axis of the water jet and intersecting the longitudinal axis of the single brush element at an acute angle, the at least one nozzle outlet directing the water jet towards the free end of the single brush element for an interaction of the water jet and the brush element at the region of the free end of the single brush element with at least a part of the water jet bypassing the free end of the brush element.

2. A cleaning nozzle as claimed in claim 1 wherein the brush element is cylindrical.

3. A cleaning nozzle as claimed in claim 1 wherein the brush element is conical.

4. A cleaning nozzle as claimed in claim 1 wherein the brush element comprises a bristle bundle with bristles extending substantially in the direction of the longitudinal axis of the brush element.

5. A cleaning nozzle as claimed in claim 4 wherein the bristle bundle comprises a tapered free end.

6. A cleaning nozzle as claimed in claim 1 wherein the brush element comprises a support extending substantially in the direction of the longitudinal axis of the brush element and bristles extending substantially radially from the support.

7. A cleaning nozzle as claimed in claim 6 wherein the bristles are arranged substantially helically around the support.

8. A cleaning nozzle as claimed in claim 1 wherein the brush element is removably secured in the nozzle body by a plug-in fitting.

9. A cleaning nozzle as claimed in claim 8 wherein the plug-in fitting extends into a recess in the nozzle body.

10. A cleaning nozzle as claimed in claim 8 wherein the plug-in fitting extends into a through-bore in the nozzle body.

11. A cleaning nozzle as claimed in claim 1 wherein said one end of nozzle body carrying the single brush element forms an angle relative to a remaining portion of the nozzle body.

* * * * *